United States Patent
Walker

(10) Patent No.: US 6,569,843 B1
(45) Date of Patent: May 27, 2003

(54) STEROIDAL SAPOGENINS FOR THE CONTROL OF COCCIDIOSIS IN ANIMALS

(75) Inventor: Reuben D. Walker, Naperville, IL (US)

(73) Assignee: Distributors Processing, Inc., Porterville, CA (US)

( * ) Notice: Subject to any disclaimer, the term of this patent is extended or adjusted under 35 U.S.C. 154(b) by 0 days.

(21) Appl. No.: 09/620,366

(22) Filed: Jul. 20, 2000

Related U.S. Application Data

(60) Provisional application No. 60/152,639, filed on Sep. 7, 1999.

(51) Int. Cl.$^7$ ............................................... A61K 31/58
(52) U.S. Cl. ....................................................... 514/173
(58) Field of Search ........................... 514/173; 424/725, 424/265.1

(56) References Cited

PUBLICATIONS

Valdez et al., "Effect of Steroidal Sapogenins on Ruminal Fermentation and on Production of Lactating Dairy Cows." J. Dairy Sci., vol. 69, pp. 1568–1575.*

* cited by examiner

*Primary Examiner*—Barbara P. Badio

(57) ABSTRACT

Steroidal sapogenins and pharmaceutically acceptable salts thereof, useful in the prevention of coccidiosis in animals and methods of administering an effective amount of steroidal sapogenin or pharmaceutically acceptable salts thereof in the diet or drinking water of the animal.

1 Claim, No Drawings

STEROIDAL SAPOGENINS FOR THE CONTROL OF COCCIDIOSIS IN ANIMALS

This application claims the benefit of Provisional application Ser. No. 60/152,639, filed Sep. 7, 1999.

BACKGROUND OF THE INVENTION

This invention relates to the use of steroidal sapogenins in the feed or water of animals to control disease (coccidiosis) caused by species of the coccidia Eimeria. Coccidiosis is a common disease in animals, resulting in intestinal lesions, diarrhea, enteritis and death. Coccidiosis is an economically important disease in domestic livestock production.

DISCLOSURE OF THE INVENTION

As a result of extensive research with plant extracts the inventor has attained the following invention. According to the present invention steroidal sapogenins extracted from plants belonging to the Lilliaceae, Amaryllidaceae and Dioscoraceae families have been discovered to effective control the damaging effects of the disease coccidoisis and its negative effects on the animal when added to the feed or water of the animal. The following examples of steroidal sapogenins extracted from plants are given merely as illustrative of the present invention and are not to be considered limiting. Agavogenin, Chlorogenin, 9-Dehydrohecogenin, 9-Dehydromanogenin, Digitogenin, Disosgenin, Gitogenin, Hectogenin, Kammogenin, Kryptogenin, Lilagenin, Manogenin, Markogenin, Mexogenin, Neotigogenin, Nologenin, Pennogenin, Rockogenin, Samogenin, Sarsasapogenin, Smilagenin, Texogenin, Tigogenin, Yamogenin and yuccagenin.

This invention is further illustrated by the following examples, which are not to be construed as imposing any limitation on the scope thereof. On the contrary, it is to be clearly understood that resort may be had various other embodiments, modifications and equivalents thereof which readily suggest themselves to those skilled in the art without departing from the spirit of the present invention and/or the scope of the appended claims.

EXAMPLE 1

A 10 day battery sensitivity trial was conducted to determine the anticoccidial activity of steroidal sapogenin in broiler chicks challenged with sporulated Eimeria tenella oocysts. Fifty, 11 day old, male Peterson X Arbor Acres, broiler chicks were placed in two foot by 3 foot pens at the rate of ten chicks per pen. A standard corn soybean meal based diet was provided with water ad libitum.

The diet were formulated to contained approximately 0, 2.84, 8.53 or 14.22 part per million of steroidal sapogenin. An inoculum containing suspensions of oocysts isolated from the field and determined to be ionophore sensitive by previous testing was used to challenge the chicks of this trial. On day 0 of the experiment each chick of the challenge treatments was inoculated with 100,00 sporulated E. tenella oocysts. The inoculum was administered by oral gavage. On day 6 all birds were sacrificed by cervical dislocation and cecal lesion scores recorded by the standard methods of Johnson and Reid on a scale of 1 to 4, with 0 representing normal intestines and 4 representing severely parasitized intestines.

| Treatment | Lesion Score | Weight Gain | Feed/Gain | Mortality, % | Dropping Score |
|---|---|---|---|---|---|
| Neg Control | 0 | 295 | 1.415 | 0 | 0 |
| Pos Control | 3.4 | 241 | 1.747 | 30 | 3.33 |
| Sapogenin-2.84 | 0.8 | 290 | 1.408 | 0 | 1.00 |
| Sapogenin-8.53 | 0.4 | 275 | 1.517 | 0 | 0.33 |
| Sapogenin-14.22 | 0.4 | 265 | 1.575 | 0 | 0.33 |

Birds in the negative control group were not infected with the E. tenella inoculum. The positive control birds were challenged with the E. tenella inoculum. The inclusion of steroidal sapogenin in the diet prevented coccidiosis mortality and significantly reduced the lesion and dropping scores caused by infection of the coccidia E. tenella. The negative effects of the coccidiosis infection on weight gain and feed per unit of weight gain were significantly reduced by the inclusion steroidal sapogenin in the diet.

EXAMPLE 2

A 7 day battery sensitivity trial was conducted to evaluate the effects of steroidal sapogenin on coccidiosis mortality, cecal lesion scores, weight gain and feed conversion in broilers challenged with sporulated E. tenella oocysts. Two hundred, 14 day old, male and female Peterson X Arbor Acres broiler chicks were assigned to twenty 2 foot by 3 foot pens at the rate of ten birds per pen. Birds were fed an standard corn soybean meal diet and water ad libitum. Diet were formulated to contain approximately 0, 0.569, 1.706 or 2.844 parts per million of steroidal sapogenin. An inoculum containing suspensions of oocysts isolated from the field and determined to be ionophore sensitive by previous testing was used to challenge the chicks of this trial. On day 0 of the experiment each chick of the challenge treatments was inoculated with 100,00 sporulated E. tenella oocysts. The inoculum was administered by oral gavage. On day 6 all birds were sacrificed by cervical dislocation and cecal lesion scores recorded by the standard methods of Johnson and Reid on a scale of 1 to 4.

| Treatment | Lesion Score | Weight Gain | Feed/Gain | Mortality, % | Dropping Score |
|---|---|---|---|---|---|
| Neg Control | 0 | 240.4 | 1.789 | 0 | 0 |
| Pos Control | 2.7 | 185.3 | 2.397 | 2.5 | 2.0 |
| Sapogenin-0.569 | 2.3 | 217.5 | 2.134 | 2.5 | 1.31 |
| Sapogenin-1706 | 1.6 | 223.4 | 2.052 | 0 | 0.94 |
| Sapogenin-2.844 | 1.5 | 212.8 | 2.133 | 0 | 1.00 |

Birds in the negative control group were not infected with the E. tenella inoculum. The positive control birds were challenged with the E. tenella inoculum. The inclusion of steroidal sapogenin in the diet at 1.706 ppm and higher prevented coccidiosis mortality and significantly reduced the lesion and dropping scores caused by infection of the coccidia E. tenella. The negative effects of the coccidiosis infection on weight gain and feed per unit of weight gain were significantly reduced by the inclusion steroidal sapogenin in the diet.

EXAMPLE 3

A 13 day coccidial challenge study was conducted with 200 Ross X Ross broiler chicks to evaluate the effects of steroidal sapogenin on coccidosis mortality, lesion scores, weight gain and feed conversion compared to a negative control, positive control, salinomycin (60 grams/ton), monensin (100 grams/ton) and steroidal sapogenin (3.32 ppm). Birds were fed a standard corn soybean meal diet and water ad libitum. Birds were placed in 4 foot by 5 foot pens at the rate of 50 birds per pen. On day 6 all birds, except the negative control, were orally challenged with an inoculum comprised of a mixture of *E. acervulina, E. maxima* and *E. tenella*. Since each of these three specie of Eimeria produce intestinal lesions in distinctly different regions of the intestinal their effects can be partitioned when scoring the birds. On day 13 all birds were sacrificed by cervical dislocation and the intestines scored for coccidial lesions by the standard Johnson and Reid method.

Average Bird Weight and Feed Conversion

| Treatment | Weight, gm | Feed/Gain |
| --- | --- | --- |
| Negative Control | 278.2 | 1.477 |
| Positive Control | 242.1 | 1.717 |
| sapogenin-3.32 ppm | 253.2 | 1.670 |
| Salinomycin-60 g/ton | 246.3 | 1.624 |
| Monensin-100 g/ton | 233.0 | 1.843 |

Steroidal sapogenin produced the highest weight gain amongst the infected birds, restoring 30.7% of the negative effects of the coccidial infection. Steroidal sapogenin was superior to both Salinomycin and Monensin the leading commercial products for control of coccidiosis infections in poultry. Steroidal sapogenin restored 19.6% of the negative effects of the coccidial infection on feed conversion. Steroidal sapogenin produced a 9.4% better feed conversion and Monensin and was 97.3% as efficient as Salinomycin.

Average Intestinal Lesion Scores

| Intestinal Region Eimeda Specie Treatment | Upper acervulina | Middle maxima | Cecal tenella |
| --- | --- | --- | --- |
| Negative Control | 0 | 0 | 0 |
| Positive Control | 2.64 | 2.38 | 2.42 |
| Sapogenin-3.32 ppm | 1.20 | 1.48 | 1.92 |
| Salinomycin-60 g/ton | 0.76 | 1.22 | 0.68 |
| Monensin-100 g/ton | 1.40 | 1.58 | 1.64 |

Steroidal sapogenin significantly ($P<0.01$) reduced average lesion scores in all regions of the intestine.

EXAMPLE 4

An 8 day coccidial challenge study was conducted with 270 day old male Arbor Acres broiler chicks to evaluate the effects of steroidal sapogenin on mortality, weight gain, feed efficiency and lesion scores. Treatments were negative control, positive control, steroidal sapogenin 1.7 ppm, steroidal sapogenin 3.4 ppm, salinomycin 60 grams/ton, monensin 90 grams/ton, and two different sources of maduramicin 5 ppm. Birds were fed a standard corn soybean meal diet and water ad libitum. Birds were placed in 5.1 sqaure foot wire battery cages at the rate of 10 birds per cages, with 3 replicate cages per treatment. On day 2 all birds, except the negative control, were orally challenged with an inoculum comprised of a mixture of *E. acervulina, E. maxima* and *E. tenella*. On day 8 all birds were sacrificed by cervical dislocation and the intestines scored for coccidial lesions by the standard Johnson and Reid method.

Effects of Steroidal Sapogenin with a Moderately Severe Infection of *E. acervulina, E. maxima* & *E. tenella*.

| Treatment | Mortality, % | Weight Gain, gm | Feed/Gain |
| --- | --- | --- | --- |
| Negative Control | 0 a | 316.33 c | 1.6297 c |
| Positive Control | 16.67 b | 225.33 e | 2.1497 d |
| Steroidal Sapogenin, 1.7 ppm | 3.33 a | 247.00 de | 1.9130 cd |
| Steroidal Sapogenin, 3.4 ppm | 0 a | 256.33 de | 1.7600 c |
| Salinomycin, 60 gm/ton | 6.67 a | 269.67 d | 1.8473 cd |
| Monensin, 90 gm/ton | 3.33 a | 258.67 d | 1.9033 cd |
| Maduramicin, 5 ppm | 0 a | 269.33 d | 1.8463 cd |
| Maduramicin, 5 ppm | 6.67 a | 266.67 d | 1.8503 cd | a,b Values in a column with different superscripts differ significantly $P < 0.025$.
c,d,e Values in a column with different superscripts differ significantly $P < 0.05$.

Steroidal sapogenin was highly effective in controlling coccidiosis mortality when faced with a moderately severe level of infection. Steroidal sapogenin tended to increase weight gains and significantly ($P<0.05$) improved feed conversion. Steroidal sapogenin controlled the negative performance effects of coccidiosis similar to the leading industry products, salinomycin, monensin and maduramicin.

Effects of Steroidal Sapogenin with Moderately Severe Infection of *E. acervulina, E. maxima* & *E. tenella*.

| | Lesion Scores | | |
| --- | --- | --- | --- |
| Treatment | Upper E. acervulina | Middle E. maxima | Cecal E. tenella |
| Negative Control | 0 a | 0 a | 0 a |
| Positive Control | 3.2667 c | 3.0333 bc | 3.1667 c |
| Steroidal sapogenin, 1.7 ppm | 2.6333 bc | 2.7667 bc | 2.6333 bc |
| Steroidal sapogenin, 3.4 ppm | 2.5667 bc | 2.6333 bc | 2.1000 b |
| Salinomycin, 60 gm/ton | 2.1333 b | 2.9000 bc | 2.9000 bc |
| Monensin, 90 gm/ton | 1.9667 b | 2.4333 bc | 2.9667 bc |
| Maduramicin, 5 ppm | 2.1000 b | 2.2667 b | 2.6000 bc |
| Maduramicin, 5 ppm | 2.3667 b | 2.3000 b | 2.3333 bc | a,b,c Values in a column with different superscripts differ significantly $P < 0.05$.

Steroidal sapogenin reduced lesion scores in all regions of the intestine and was more effective than industry standard products in controlling cecal lesion scores caused by *E. tenella*.

EXAMPLE 5

An anticoccidal product must be compatible with commonly used antibiotics to to have practical application in livestock production. To evaluate the compatibility of steroidal sapogenin with three widely used poultry antibiotics. A total of 360 Ross×Ross 308 mixed sex chicks were utilized in a 14 day coccidial challenge study. Antibiotics tested were the combination of Bacitracin MD plus Roxarsone, Virginiamycin and Bacitracin Zinc. On day 7 of the study all birds except the negative control received an oral challenge of a mixed culture of *E. acervulina, E. maxima* and *E. tenella*. On day 14 all birds were sacrificed by cervical dislocation and the intestines scored for coccidial lesions by the standard procedure.

Steroidal Sapogenin and Antibiotic Compatibility

| Treatment | Lesion Scores | | | Weight, gm | Feed/Gain |
| | Upper | Middle | Cecal | | |
|---|---|---|---|---|---|
| Negative Control | 0 a | 0 a | 0 a | 250.6 ab | 1.910 abc |
| Positive Control | 1.42 b | 2.17 d | 1.42 b | 188.2 c | 2.216 ab |
| Steroidal Sapogenin, 3.3 ppm | 0.08 a | 0.42 a | 0.17 a | 230.2 b | 2.039 abc |
| BMD + Roxasone | 1.42 b | 1.25 bc | 1.50 b | 161.0 c | 2.233 a |
| BMD + Roxasone + SS-3.3 ppm | 0.33 a | 0.75 ab | 0.08 a | 181.4 c | 1.959 abc |
| Virginiamycin | 1.17 b | 1.58 cd | 1.17 b | 256.3 ab | 1.891 abc |
| Virginiamycin + SS-3.3 ppm | 0.25 a | 1.25 bc | 0.33 a | 271.0 a | 1.780 c |
| Bacitracin Zinc | 1.50 b | 2.08 d | 1.50 b | 259.7 ab | 1.833 bc |
| Bacitracin Zinc + SS-3.3 ppm | 0.25 a | 1.17 bc | 0.17 a | 248.1 ab | 2.054 abc | abc Values within a column having different superscripts differ significantly $P < 0.05$.

Steroidal sapogenin was highly effective in controlling the negative effects of coccidial infection on lesion scores, weight gain and feed efficiency when fed alone or in combination with the tested antibiotics. Saperoidal sapogenin had no effect on the function of the antibiotic and the antibiotics had no effects upon the anticoccidial efficacy of steroidal sapogenin.

EXAMPLE 6

Anticoccidal products must be safe for the animal fed the product to have any practical applications in livestock production. Many of the existing commercial anticoccidial products have a low margin of safety between the recommended usage level and levels that are toxic to the animal. To evaluate the safety of steroidal sapogenin an acute oral toxicity study was conducted with laboratory rats. Rats were orally dosed with 0, 15.27, 30.54 and 61.07 mg/kg live body weight of steroidal sapogenin and observed for 14 days. There were no deaths nor adverse reactions in any individual rat.

To evaluate the safety of steroidal sapogenin in broiler chickens a total of 200 Ross×Ross 308 mixed sex chickens were fed 0, 3.32, 9.96 or 33.21 ppm steroidal sapogenin for a complete 42 day growth cycle.

Steroidal Sapogenin—42 Day Safety

| Treatment | Weight, kg | Feed Intake, gm/Day | Feed/Gain |
|---|---|---|---|
| Control | 4.462 | 212.05 | 1.996 |
| Steroidal Sapogenin 3.32 ppm | 4.705 | 221.36 | 1.976 |
| Steroidal Sapogenin 9.96 ppm | 4.605 | 218.19 | 1.990 |
| Steroidal Sapogenin 33.21 ppm | 4.535 | 212.28 | 1.966 |

There was no significant difference in mortality between the control and any of the steroidal sapogenin treatment levels. All dose levels produced increased weight gains and improved feed efficiency compared to the controls. Livers of the birds were sent to Virigina Poloytechnic Institute College of Veterinary Medicine's Poultry Pathology Laboratory where extensive histopathology test were conducted. There were no liver lesions or any disease involving the liver of these birds.

EXAMPLE 7

Anticoccidial products must be stable for temperatures normally encountered in the manufacture of animal feeds and stable to long storage. To evaluate the temperature stability of steroidal sapogenin under pelleting, extruding and expanding manufacturing conditions samples of steroidal sapogenin were exposed to 149 C (300 F) for 0, 2.5, 5.0 and 10 minutes and the percent of recovered steroidal sapogenin determined.

| Time | Steroidal Sapogenin, ppm | % |
|---|---|---|
| 0 | 16,288 | 100.00 |
| 2.5 | 16,547 | 101.59 |
| 5.0 | 16,288 | 100.00 |
| 10.0 | 16,288 | 100.00 |

Steroidal sapogenin is highly stable to feed manufacturing conditions. Exposure of steroidal sapogenin to pelleting, extruding or expanding temperatures should have no negative affects on the efficacy of steroidal sapogenin.

To evaluate the stability of steroidal sapogenin under long term storage conditions a series of different samples were stored at 22 C (72 F) for 0, 12 and 24 months.

| Months | Steroidal Sapogenin, ppm | % |
|---|---|---|
| 0 | 21,274 | 100 |
| 12 | 20,632 | 96.98 |
| 24 | 20,698 | 97.29 |

Steroidal sapogenin is highly stable under normal storage conditions for animal feed products with less than 3% loss of activity over 24 months.

EXAMPLE 8

The greatest weakness of all existing commercial anticoccidial products is the tendency for coccidia to develop resistance to the active compound, significantly decreasing the effectiveness of the compound to control the negative effects of coccidiosis infections. Coccidial resistance is developed when the coccidia are continuously exposed to a compound over a long period of time. To evaluate the potential for coccidia to develop resistance to steroidal sapogenin three consecutive flocks of broilers were fed steroidal sapogenin. Lesion scores were collected every 14 days over the 18 week study to compare the effects of the steroidal sapogenin compared to the control flock.

| Section | Flock | Control | Treatment | Difference |
| --- | --- | --- | --- | --- |
| Upper | 1 | 1.133 | 0.733 | −0.400 |
| Upper | 2 | 0.933 | 0.267 | −0.666 |
| Upper | 3 | 1.333 | 0.600 | −0.733 |
| Middle | 1 | 2.000 | 0.800 | −1.200 |
| Middle | 2 | 1.200 | 0.200 | −1.000 |
| Middle | 3 | 1.400 | 0.400 | −1.000 |
| Cecal | 1 | 1.333 | 0.667 | −0.666 |
| Cecal | 2 | 0.933 | 0.333 | −0.600 |
| Cecal | 3 | 1.000 | 0.200 | −0.800 |
| Total | 1 | 4.467 | 2.200 | −2.267 |
| Total | 2 | 3.067 | 0.800 | −2.267 |
| Total | 3 | 3.733 | 1.200 | −2.533 |

Steroidal sapogenin significantly ($P<0.001$) reduced lesion scores in all regions of the intestine with no loss of efficacy on the 18 week study.

Data presented in the present invention are illustrative of the efficacy of steroidal sapogenin in controlling the effects of Eimeria. These examples with species of Eimeria in broilers are not to be considered limited to these species of Eimeria nor animal species.

On the basis of the above results, it is obvious that steroidal sapogenin is effective in controlling the negative effects of coccidial infection (coccidiosis) in animals.

What is claimed is:

1. A method of controlling coccidiosis in animals comprising of administering to an animal an effective amount of steroidal sapogenin.

\* \* \* \* \*